United States Patent
Cheng et al.

(10) Patent No.: US 11,116,463 B2
(45) Date of Patent: Sep. 14, 2021

(54) APPARATUS WITH FLEXIBLE X-RAY GRATINGS

(71) Applicant: The Board of Trustees of the Leland Stanford Junior University, Stanford, CA (US)

(72) Inventors: Yao-Te Cheng, Sunnyvale (CA); Ludwig Galambos, Menlo Park, CA (US); Lambertus Hesselink, Atherton, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 94 days.

(21) Appl. No.: 16/738,807

(22) Filed: Jan. 9, 2020

(65) Prior Publication Data

US 2020/0222017 A1 Jul. 16, 2020

Related U.S. Application Data

(60) Provisional application No. 62/791,357, filed on Jan. 11, 2019.

(51) Int. Cl.
*A61B 6/00* (2006.01)
*G21K 1/06* (2006.01)

(52) U.S. Cl.
CPC ............ *A61B 6/484* (2013.01); *A61B 6/4035* (2013.01); *A61B 6/4291* (2013.01)

(58) Field of Classification Search
CPC ............ G21K 1/04; G21K 1/06; G21K 1/067; G21K 2201/064; H01L 41/0986; A61B 6/4291; A61B 6/0414; A61B 6/484; A61B 6/502
See application file for complete search history.

(56) References Cited

U.S. PATENT DOCUMENTS

| 9,970,119 B2 | 5/2018 | Yokoyama |
| 2011/0052800 A1 | 3/2011 | Setomoto et al. |
| 2018/0294065 A1* | 10/2018 | Martens ................... G21K 1/06 |

OTHER PUBLICATIONS

Joachim N. Burghartz, "Make Way for Flexible Silicon Chips", Feb. 25, 2013, https://spectrum.ieee.org/semiconductors/materials/make-way-for-flexible-silicon-chips, Nov. 22, 2019.
(Continued)

*Primary Examiner* — Don K Wong
(74) *Attorney, Agent, or Firm* — Beyer Law Group LLP

(57) ABSTRACT

An X-ray grating configured for use in an X-ray imaging apparatus is provided. The X-ray grating has a silicone-based base layer. A plurality of silicon-based ridges is on a surface of the silicon-based base layer, wherein the plurality of silicon-based ridges from a plurality of trenches, where a trench of the plurality of trenches is between two silicon-based ridges of the plurality of silicon-based ridges. A plurality of silicon-based bridges extends between adjacent silicon-based ridges, wherein each silicon-based ridge of the plurality of silicon-based ridges is connected to at least one adjacent silicon-based ridge of the plurality of silicon-based ridges by at least one of a silicon-based bridge of the plurality of silicon-based bridges and wherein at least one of a plurality of four adjacent trenches does not have any silicon-based bridges.

24 Claims, 10 Drawing Sheets

(56) References Cited

OTHER PUBLICATIONS

Joachim N. Burghartz, "Ultra-thin Chip Technology and Applications", New York, NY, Spring Science+Business Media, LLC, 2011.
Gupta et al., "Ultra-thin chips for high-performance flexible electronics", https://www.nature.com/articles/s41528-018-0021-5, Mar. 14, 2018.

* cited by examiner

APPARATUS WITH FLEXIBLE X-RAY GRATINGS

CROSS-REFERENCE TO RELATED APPLICATION

This application claims the benefit of priority of U.S. Application No. 62/791,357, filed Jan. 11, 2019, which is incorporated herein by reference for all purposes.

GOVERNMENT RIGHTS

This invention was made with Government support under contracts HSHQDC-12-C-00002 and HSHQDC-17-C-00053 awarded by US Department of Homeland Security, Science and Technology Directorate Explosives Division and HSTS04-17-C-CT7224 awarded by Transportation Security Administration. The Government has certain rights in the invention.

BACKGROUND

This disclosure relates generally to X-ray imaging. More specifically, the disclosure relates to differential phase contrast (DPC) gratings for X-ray imaging.

SUMMARY

In accordance with the invention, an X-ray grating configured for use in an X-ray imaging apparatus is provided. The X-ray grating has a silicon-based base layer. A plurality of silicon-based ridges is on a surface of the silicon-based base layer, wherein the plurality of silicon-based ridges form a plurality of trenches, where a trench of the plurality of trenches is between two silicon-based ridges of the plurality of silicon-based ridges. A plurality of silicon-based bridges extends between adjacent silicon-based ridges, wherein each silicon-based ridge of the plurality of silicon-based ridges is connected to at least one adjacent silicon-based ridge of the plurality of silicon-based ridges by at least one of a silicon-based bridge of the plurality of silicon-based bridges and wherein at least one of a plurality of four adjacent trenches does not have any silicon-based bridges.

In another manifestation, an X-ray grating configured for use in an X-ray imaging apparatus is provided. A silicon-based base layer has a thickness of no more than 70 microns. A plurality of silicon-based ridges is on a surface of the silicon-based base layer, wherein a trench of a plurality of trenches is between a pair of adjacent silicon-based ridges of the plurality of silicon-based ridges.

In another manifestation, a method of forming an X-ray grating is provided. A silicon-based substrate is etched to form a plurality of silicon-based ridges with trenches between the plurality of silicon-based ridges, and forming a base layer, wherein the plurality of silicon-based ridges is connected to the base layer and wherein the base layer has a thickness of no more than 70 microns.

The invention and objects and features thereof will be more readily apparent from the following detailed description and appended claims when taken with the drawings.

DETAILED DESCRIPTION OF ILLUSTRATED EMBODIMENTS

X-ray differential phase contrast (DPC) imaging uses an X-ray imaging system utilizing an X-ray interferometer to detect the changes in the X-ray phases when X-rays propagate through objects. Most of the X-ray phase contrast imaging techniques require either a synchrotron radiation X-ray source or a relatively weak micro-focused X-ray source. A three-grating based X-ray DPC imaging system provides a solution of using a more commonly used large spot X-ray source and large pixel-size X-ray detectors.

Figure 1:
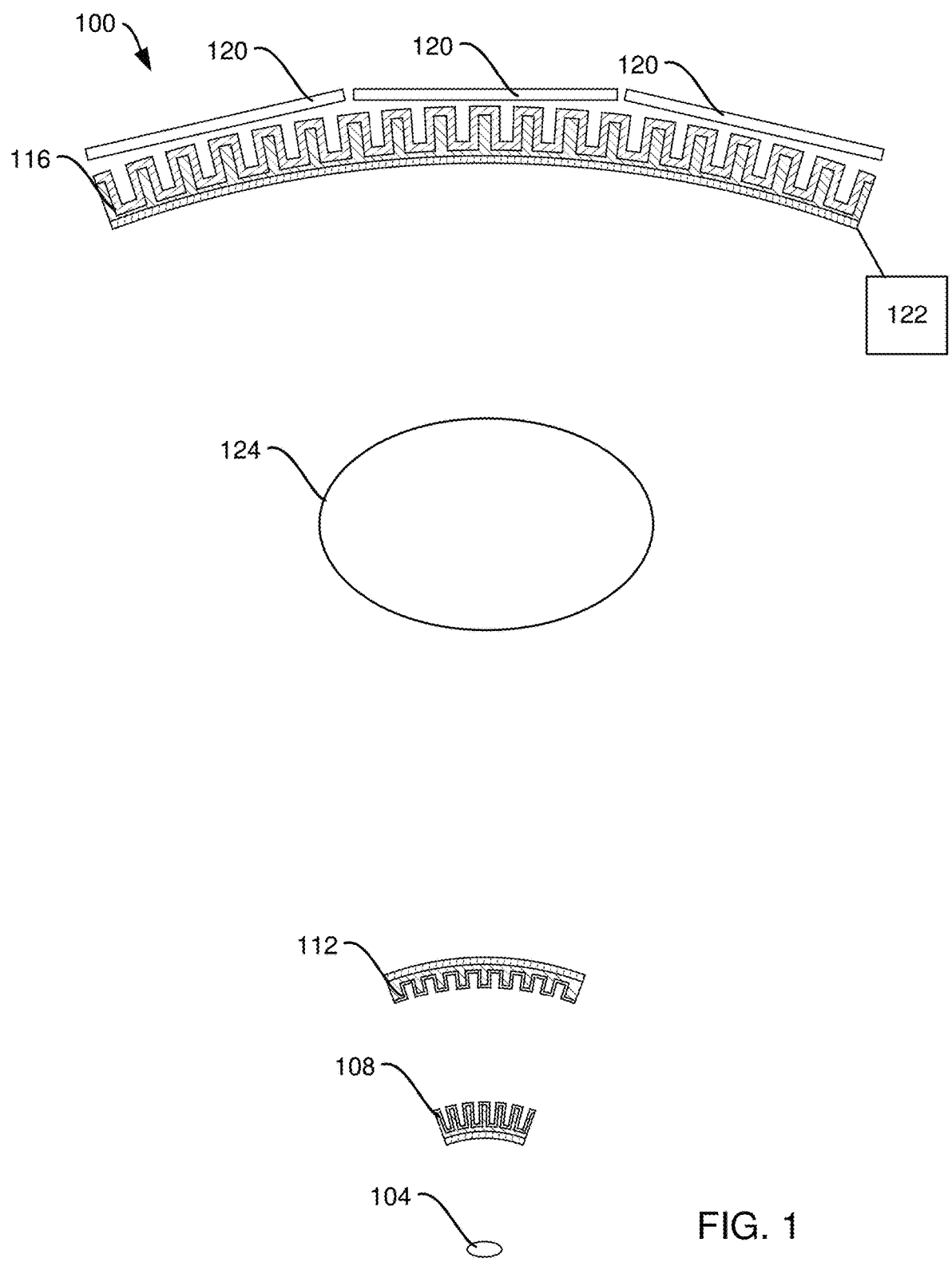
FIG. 1 is a schematic view of an embodiment of an X-ray imaging apparatus, such as an X-ray DPC imaging system.

FIG. 1 is a schematic view of an embodiment of an X-ray imaging apparatus, such as an X-ray DPC imaging system 100. The X-ray DPC imaging system comprises an X-ray source 104, a first grating 108, a second grating 112, a third grating 116, and an X-ray detector 120. An object 124 to be imaged is placed between the second grating 112 and the third grating 116. In the same way, the first grating 108, second grating 112, third grating 116, and X-ray detector 120 extend out of the page. A motor 122 is mechanically connected to the third grating 116 and is adapted to shift the third grating 116 by portions of the pitch p2. In other embodiments, the object 124 may be placed between the first grating 108 and the second grating 112. In other embodiments, a mechanical motor 122 is not used.

To have sufficient spatial coherence to form the X-ray interference fringes, the X-ray source 104 usually needs to smaller than 10 μm (depending on the interferometer design, ex: X-ray energy and spacing between X-ray source, gratings, and detectors). However, most of the X-ray sources used in the commercial computed-tomography (CT) scanners for aviation security and medical imaging have a source spot ranging from a few hundred micrometers to a few millimeters. The first grating 108, source amplitude gratings (G0), with pitch p0, can be used in front of the X-ray source to filter a big extended X-ray source to effectively multiple thin-slit X-ray line sources. The pitch (or called period), a constant spacing between each of the thin slits, can be designed such that the X-ray fringes formed from each of the thin slits source of the first grating 108 overlap completely at the position of the third grating 116.

Before an object 124 is inserted in the X-ray DPC imaging system 100, a periodic X-ray interference fringe pattern is formed right in front of the X-ray detector 120. When an object 124 is inserted in the X-ray beam path, a few things happen, which change the X-ray interference fringe patterns. Part of the X-rays is absorbed by the object 124, which reduce the intensity of the X-ray fringes. Part of the X-ray wavefront is modified by the object 124 because the object has different refractive indices compared to air, which changes the phases of the X-ray wavefront at the X-ray fringes and changes the lateral positions of the fringe pattern locally. Part of the X-rays is scattered off of the object 124, which modifies the X-ray fringe's amplitude. Depending on the X-ray interferometer designs, the pitch of the X-ray fringes in front of the X-ray detector 120 is on the scale of micrometers. However, pixel sizes of commercially available X-ray detectors usually range from tens of micrometers to a few millimeters. It is not possible to detect the position changes in the X-ray fringe pattern with detectors having such big pixels. To discover the position changes of the X-ray fringe patterns, the third grating 116, analyzer amplitude gratings (G2), with a pitch p2, is placed right in front of the X-ray detector 120. The third grating 116 has the same pitch (or period) as the X-ray fringe's pitch in front of the X-ray detector 120. If all of the bright fringes (where the maximum X-ray intensity is located) are aligned with the third grating 116 open slits, the X-ray detector 120 would get an integrated "high" signal. On the other hand, if all of the dark fringes (where the minimum X-ray intensity is located) are aligned with the third grating 116 open slits, the detector would get an integrated "low" signal. Conventionally, a phase stepping by shifting the third grating 116 laterally by portions of one period (pitch) using a motor 122 will lead to a series of detected signals. By fitting the curves the X-ray fringe pattern's intensity ($I_0$), amplitude (A) and phase ($\phi$) can be extracted.

By comparing the parameters of the reference fringe patterns (when no objects are in the beam path) and the fringe patterns having objects, three different X-ray images can be obtained according to the following equations:

Absorption image=$I_{0,\ obj}/I_{0,\ ref.}$ (equivalent to the traditional X-ray images)

Differential phase contrast image=$\phi_{obj.}-\phi_{ref.}$

Dark-field image=$(A_{obj}/I_{0,\ obj.})/(A_{ref}/I_{0,\ ref.})$

The function of an amplitude grating (such as the first grating 108 and the third grating 116) is to allow part of the X-rays to propagate through the open slits while significantly blocking the rest of the X-rays. X-ray amplitude gratings are usually made of gold because gold can absorb X-rays efficiently. Therefore, a G0 source amplitude grating of a finite thickness would significantly block X-rays emitting at large angles while the amplitude grating itself also acts like an X-ray collimator, which limits the X-ray emission angle to roughly $\theta_{FOV,\ G0}$ (=G0 thickness/(G0 pitch/2)). For high energy X-ray DPC imaging systems, the requirement of gold thickness to make G0 and G2 proper amplitude gratings can be as high as tens of micrometers to hundreds of micrometers. With a micrometer-sized grating slit opening, the $\theta_{FOV,\ G0}$ can be a few degrees to even less than one degree. For a fan-beam or a cone-beam X-ray imaging system, the amplitude gratings would significantly reduce the imaging field-of-view (FOV) from only a few centimeters to a few millimeters wide for, for example, a source-to-detector distance of less than 2 meters.

In order to implement X-ray gratings on an X-ray CT scanner having an angular FOV of ~70 degrees, (curved) cylindrical first, second, and third gratings 108, 112, 116 are needed, where all gratings are centered at the X-ray source 104. In this embodiment, the X-rays can transmit through all of the grating slits nearly in parallel. Therefore, the X-rays can be detected at the detectors located at the full field of view.

Most silicon-based devices are made on planar surfaces, using readily available fabrication devices and techniques. Device fabrication on curved surfaces presents a significant challenge because flat silicon wafers are typically hundreds of microns thick and rigid. Various embodiments provide silicon substrates with a flexible base layer.

There are multiple options of choosing the second grating 112 between π-phase shift or π/2-phase shift, and there are also multiple options of utilizing different orders of Talbot self-images to locate the G2 analyzer gratings. One common solution (π-phase shift G1 with first-order Talbot self-image) among all possible solutions is used to explain the design rules.

One of the line sources, extended in and out of the page, located immediately after the first grating 108 is formed by filtering the original X-ray source 104 with the first grating 108. The first grating 108 is located with a distance l in front of the second grating 112, which is a π-phase shift G1 grating (with a pitch of $p_1$). A Talbot self-image of the diffracted X-ray fringes shown at $d=(l+d)/l*p_1^2/(8\lambda)$ is obtained after the second grating 112. The fringe pitch is equal to $(l+d)/l*p_1/2$. By solving the equation $d=(l+d)/l*D_1$, where $D_1=p_1^2/(8\lambda)$ two solutions: $l=s/2\pm sqrt(s^2/4-sD_1)$ can be obtained, where s=l+d and is the distance between the first grating 108 and the third grating 116. These two solutions mean that solutions can be selected to have the distance between G0 and G1 longer than the distance between G1 and G2 or the other way around. Finally, when a solution is chosen, a simple geometry relation is used to decide the pitch of the G0 grating by $p_0=(l/d)*p_2$.

The X-ray DPC imaging system's parameters are determined by the wavelength ($\lambda$) of the X-rays and therefore determined by the energy (E) of the X-rays by $E=(h*c)/\lambda$, where h is the Planck constant and c is the speed of light.

In addition to the system's dimension, the selection of the designed energy for the X-ray DPC imaging system is usually decided by different applications. The wavelength ($\lambda$), and therefore the energy of X-rays is described for monochromatic X-rays by the previously mentioned equations. For a typical commercially available polychromatic X-ray source, the equations are still useful to design a polychromatic X-ray DPC imaging system. Usually, the design energy (or wavelength) described in those equations is close to the mean energy (or wavelength) of an X-ray source or an X-ray system. This design energy can be obtained through optimization of the resulting fringe contrast using well-known design principles in the art. For applications focused on relatively small objects or low-absorptive materials such as mammography and dental X-rays, X-rays do need to penetrate the small objects. Relatively low mean X-ray energies, such as less than 40 keV, may be used. On the other hand, for big objects with more absorptive materials, such as aviation security CT scanners, a much higher mean X-ray energy would be needed, ex: 90-100 keV.

Figure 2:
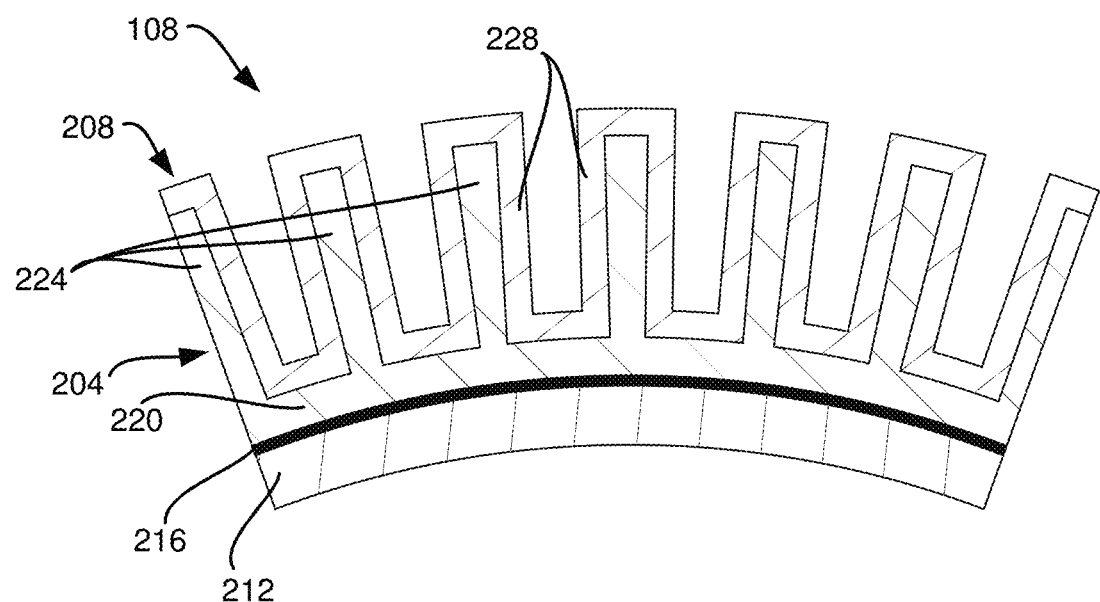
FIG. 2 is an enlarged view of a first grating.

FIG. 2 is an enlarged view of the first grating 108. In this embodiment, the first grating is an amplitude grating. The first grating 108 comprises a silicon substrate 204, a metal layer 208 on the silicon substrate 204, and a mounting substrate 212 with a curved surface, where the silicon substrate 204 is attached to the curved surface of a mounting substrate 212, by an adhesive 216. The silicon substrate 204 comprises a silicon base layer 220, which is attached to the curved surface of the mounting substrate 212 and a plurality of silicon ridges 224 attached to the silicon base layer 220 and extending radially from the silicon base layer 220. The metal layer 208 has radially extending portions 228 on sidewalls of the silicon ridges 224, which extend between the silicon ridges. In this embodiment, each silicon ridge 224 provides two radially extending portions 228 of the metal layer 208.

Figure 3:
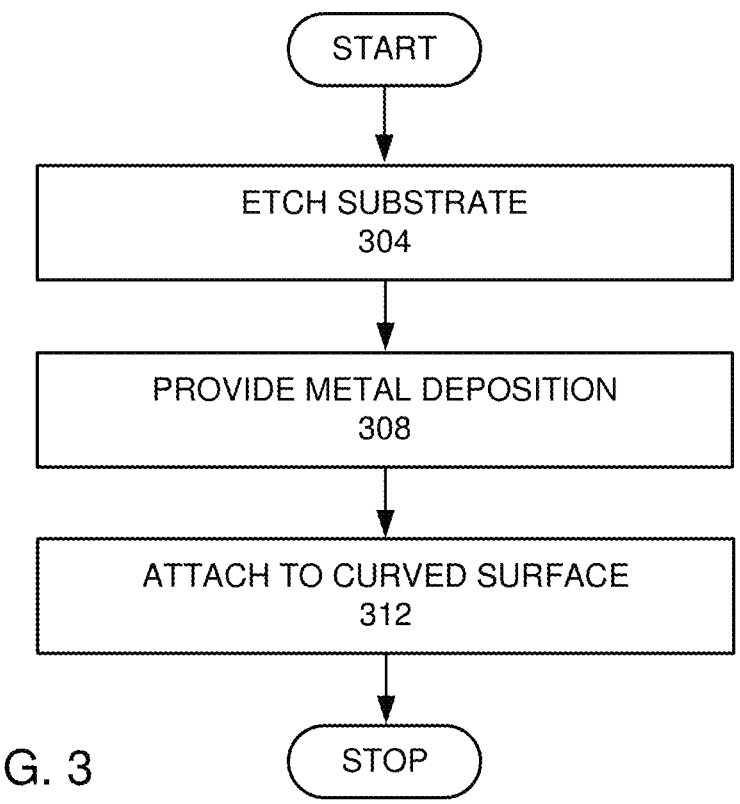
FIG. 3 is a high level flow chart of a process that is used to form the first grating in an embodiment.

FIG. 3 is a high level flow chart of a process that is used to form the first grating 108 in an embodiment. A substrate is etched (step 304). In one embodiment, a deep reactive ion etching (DRIE) is used to etch trenches in a silicon wafer followed by using a potassium hydroxide (KOH) wet etching to thin the other side of the silicon wafer until the grating base layer is less than 70 μm. In other embodiments, the trenches may also be etched by wet processes like KOH etching on the front side, too.

Figure 4A:
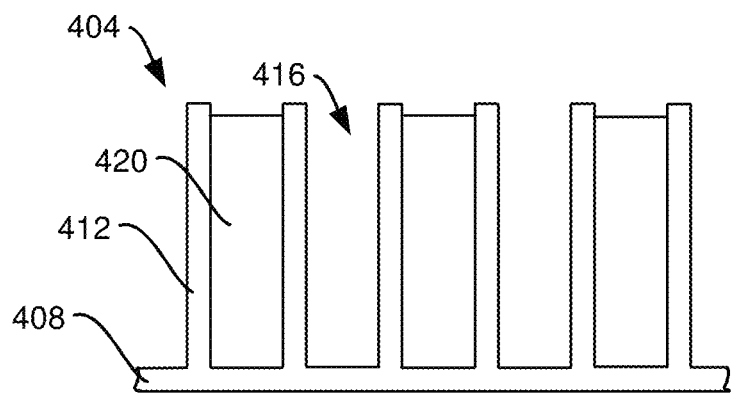
FIGS. 4A-B are enlarged cross-sectional side views of part of a silicon substrate that has been processed in an embodiment.
Figure 5A:
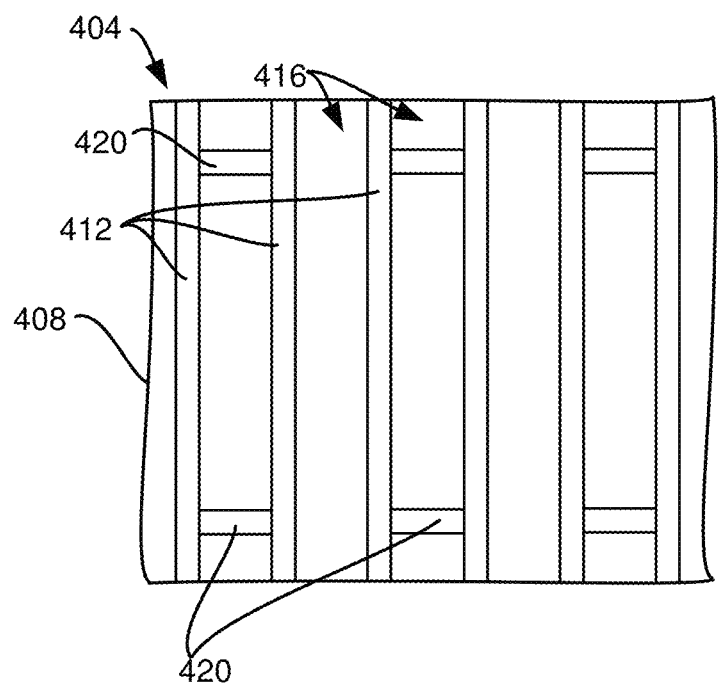
FIGS. 5A-B are schematic top views of the silicon substrate, shown in FIGS. 4A-B.

FIG. 4A is an enlarged cross-sectional side view of part of a silicon substrate 404 that has been etched in an embodiment. FIG. 5A is a schematic top view of the silicon substrate 404. The etching of the substrate (step 304) forms the substrate into a silicon base layer 408 with a plurality of silicon ridges 412 attached to the silicon base layer. In this example, the etching of the silicon substrate 404 forms trenches 416 between the silicon ridges 412. Bridges 420 are formed between adjacent silicon ridges 412. The bridges 420 are shown to be slightly lower than the silicon ridges 412. However, in various embodiments, the bridges 420 and silicon ridges 412 may be the same height. In this embodiment, each silicon ridge 412 is connected to only one other adjacent silicon ridge 412, so that every other trench does not have a bridge 420. In an embodiment, the etching the substrate (step 304) may be a single etch that etches the trenches 416. In another embodiment, a first etch on a first side of the silicon substrate 404 etches the trenches 416 into the silicon substrate 404 and a second etch that etches the other side of the silicon substrate 404 that further thins the silicon base layer 408. In another embodiment, a polishing or machining process may be used to etch the second side of the silicon substrate 404 to further thin the silicon base layer 408. In this embodiment, the silicon base layer 408 has a thickness of no more than 70 microns.

Figure 4B:
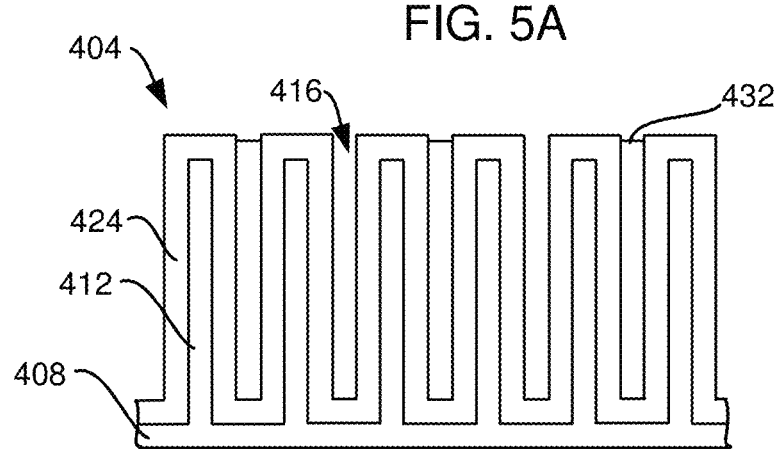
Figure 5B:
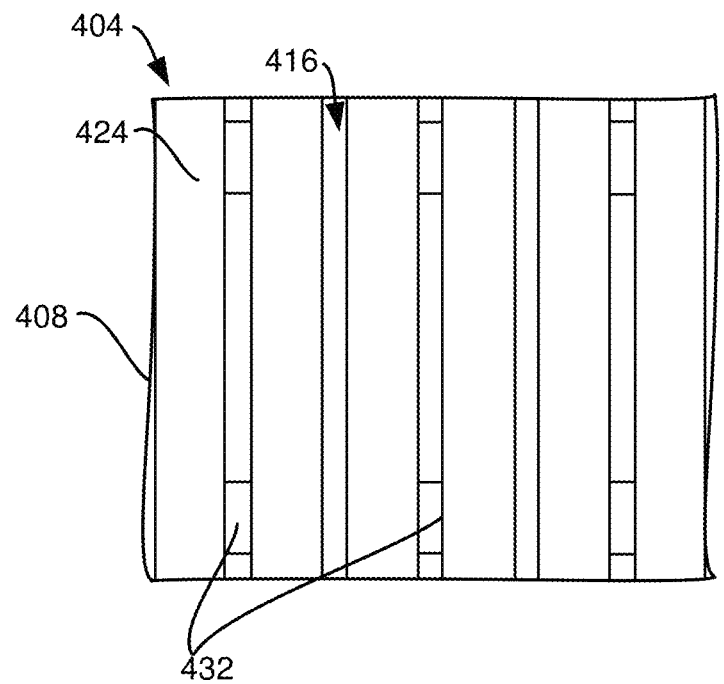

A metallic deposition is formed between the silicon ridges 412 (step 308). In this embodiment, a chromium adhesion layer and a gold seed layer is first deposited with sputtering followed by conformal electroplating of gold on the silicon substrate 404. In other embodiments, the metallic deposition may be deposited by one of various methods, such as electroplating, sputtering, or atomic layer deposition. In this embodiment, electroplating is used to deposit a gold layer. In other embodiments, lead, platinum, tungsten, or nickel may be deposited. FIG. 4B is an enlarged cross-sectional side view of part of a silicon substrate 404 after a gold layer 424 has been deposited between the silicon ridges 412. FIG. 5B is a schematic top view of the silicon substrate 404. In this embodiment, the metallic deposition of a gold layer 424 forms a metallic conformal layer with trenches or spaces between vertical sections of the gold layer 424. The gold layer 424 forms a bridge covering 432 over the silicon bridges.

The silicon base layer 408 is attached to a curved surface by an adhesive (step 312). After electroplating, a laser cutter may be used to cut the base-thinned first grating 108 out of the silicon wafer and mount it on a mounting substrate. In general, a thick silicon wafer larger than 300 μm is very rigid and brittle when trying to bend it. A silicon wafer/chip starts to be more and more flexible when it is thinned down below 70 micrometers. Since the silicon base layer 408 is no more than 70 microns thick, an adhesive alone, without additional mechanical clamps may be used to attach the silicon base layer 408 to a curved surface with a radius of curvature of less than 50 cm. Preferably, the silicon base layer 408 has a thickness of between 0.5 microns to 50 microns. In some embodiments, the adhesive may be photoresist, spin-on glass, or epoxy glues.

In this embodiment, the pitch of the vertical parts of the gold layer 424 has half the pitch (period) of the silicon ridges 412. This is because each silicon ridge 412 is used to provide two vertical parts of the gold layer 424. As a result, the trenches may be etched with a pitch that is twice the pitch (period) of the desired grating. In some embodiments, an adhesion layer, such as chromium, titanium, titanium oxide, germanium, or aluminum oxide may be deposited as a binder between the silicon substrate and the deposited metal.

In this embodiment, the silicon bridges 420 are provided between the silicon ridges 412, where each silicon ridge 412 is connected to only one adjacent silicon ridge 412 and where every other trench 416 does not have a silicon bridge 420. The silicon bridges 420 provide more stability between silicon ridges 412 significantly reducing the deformation of the silicon ridges 412. A plurality of silicon bridges 420 connects adjacent silicon ridges 412 along the length of the silicon ridges 412 to reduce deformation along the length of the silicon ridges 412. If the spacing between the silicon bridges 420 is too great, deformation increases. In an embodiment, the spacing between silicon bridges 420 is less than 200 microns. Trenches 416 without silicon bridges need to be provided periodically in order to allow the silicon base layer 408 to be curved.

Alignment fiducial marks may be built into the X-ray grating pattern which can be used for future grating alignment in the X-ray imaging system. This is basically to make alignment marks into the X-ray grating structure.

In some embodiments, at least part of the silicon substrate may have a dielectric layer (i.e. silicon dioxide, silicon nitride or diamond) or a metallic layer (i.e. chromium, titanium or gold). For example, additional dielectric layers may be used as an insulation layer to prevent metal from being electroplated on the backside of the grating during electroplating. In another example, additional metallic layers may be used as a high heat conduction layer to dissipate heat generated during X-ray imaging. In another example, additional dielectric layers may be used as an etch stop in step 304.

In some embodiments, the top of the gratings may be covered with a dielectric layer or a metallic layer to be used as a protection layer that covers the active electroplated metal gratings. In some embodiments, the grating trenches may be filled and covered with additional protection layers such as photoresist, spin-on-glass, polydimethylsiloxane (PDMS), or epoxy glues. The protection layer may protect the grating trenches from being filled with dust or particles during X-ray operation, which may damage the X-ray gratings or affect the image quality.

For the X-ray DPC imaging system 100, there are multiple options of choosing the second grating 112, a G1 phase grating, between π-phase shift or π/2-phase shift, and there are also multiple options of utilizing different orders of Talbot self-images to locate the third grating 116, a G2 analyzer grating. For example, one common solution is a π-phase shift G1 with first-order Talbot self-image, among all possible solutions to explain the design rules. In an example, 28 keV X-rays are used.

This embodiment can be readily applied in silicon processing facilities and may be implemented for mass, low-cost manufacturing. In an embodiment, it has been found that standard manufacturing processes may be used to obtain a precision of 0.5% in successfully forming gratings.

Figure 6:
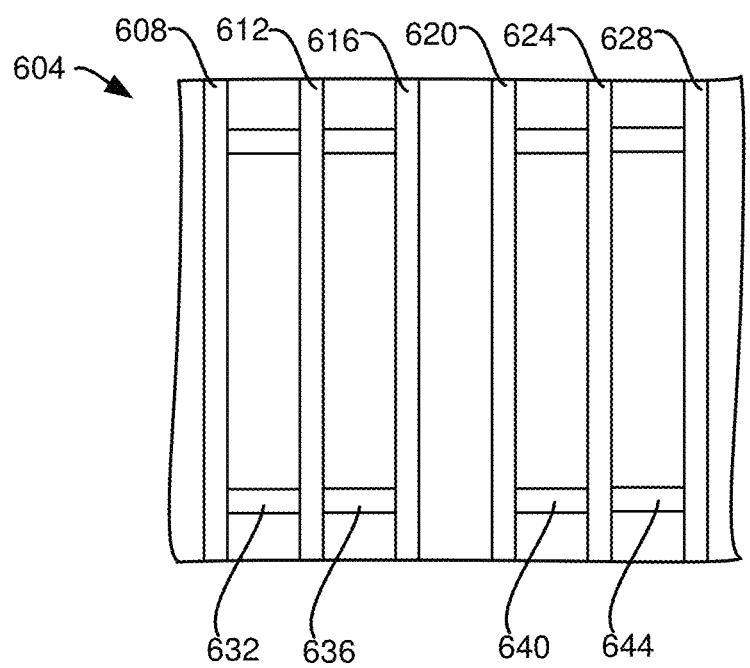
FIG. 6 is a schematic top view of an enlarged section of an etched silicon substrate in another embodiment.

FIG. 6 is a schematic top view of an enlarged section of an etched silicon substrate 604 in another embodiment. The silicon substrate has a first silicon ridge 608, a second silicon ridge 612, a third silicon ridge 616, a fourth silicon ridge 620, a fifth silicon ridge 624, and a sixth silicon ridge 628. A first bridge 632 connects the first silicon ridge 608 to the second silicon ridge 612. A second bridge 636 connects the second silicon ridge 612 to the third silicon ridge 616. A third bridge 640 connects the fourth silicon ridge 620 to the fifth silicon ridge 624. A fourth bridge 644 connects the fifth silicon ridge 624 to the sixth silicon ridge 628. Instead of pairs of silicon ridges being connected together, triplets of silicon ridges are connected together by bridges. For each triplet of silicon ridges, two silicon ridges are only connected to one adjacent silicon ridge and one silicon ridge is connected to two adjacent silicon ridges. In this example, two out of every three silicon ridges are connected to only one adjacent silicon ridge. In addition, in this embodiment, every third trench does not have any bridges. Therefore, when the silicon base layer is bent, every third trench without bridges allows the silicon base layer to bend.

In various embodiments, at least every fourth silicon ridge is connected to only one adjacent silicon ridge. Therefore, in various embodiments, every first, second, third or fourth silicon ridge of the plurality of silicon ridges is connected to only one adjacent silicon ridge by at least one silicon bridge. In such embodiments, first silicon ridges may be connected to only one other silicon ridge and then later third silicon ridges may be connected to only one other silicon ridge. Therefore, in various embodiments, every second, third, fourth, or fifth trench does not have any bridges.

In various embodiments, the silicon ridges form equally spaced parallel lines having a constant pitch. In other embodiments, the silicon ridges form unequally spaced parallel lines having a varying pitch. In other embodiments, the silicon ridges form equally spaced and evenly spaced non-linear curves. In other embodiments, the silicon ridges form unequally spaced and evenly spaced non-linear curves. Evenly spaced non-linear curves are defined as being where two curves are spaced approximately the same distance from each other along the length of the curves.

The thinness of the silicon base layer allows for a radius of curvature of less than 15 cm when the silicon base layer is held by adhesive without clamps. In various embodiments, the radius of curvature is between 6 to 10 cm. Other embodiments provide a radius of curvature of less than 5 cm by using adhesive without clamps. Other embodiments have a radius of curvature of less than 3 cm by using adhesive to glue onto a curved surface without clamps. In various embodiments, the silicon ridges have a thickness of at least 3 microns. In other embodiments, the silicon ridges have a thickness of at least 100 microns. In various embodiments, the silicon base layer is bent to have a radius of curvature of less than 17 cm. In other embodiments, the silicon base layer is bent to have a radius of curvature of less than 37 cm. In other embodiments, the silicon base layer is bent to have a radius of curvature of less than 1.55 m.

In various embodiments, the silicon ridges have a constant pitch. In other embodiments, the silicon ridges have a varying pitch. Various embodiments design bridges to minimize shadowing created by the bridges. The bridges are most helpful when the silicon ridges have a width of less than 5 microns or a height to width ratio of greater than 20:1. In various embodiments, the silicon ridges have a height and width, wherein a ratio of the height to the width is greater than 5:1. In this embodiment, the silicon bridges have a width that is between 0.1 to 10 times the width of the silicon ridges. In this embodiment, the length of the bridges is perpendicular to the length of the silicon ridges. The silicon bridges are spaced as far apart as possible along the length of the silicon ridges without resulting in silicon ridge deformation beyond a certain tolerance. A block of silicon ridges may be defined as a group of silicon ridges joined by bridges between trenches without any bridges. As mentioned before, various embodiments may have two, three, or four silicon ridges in a block of silicon bridges. If the block of silicon ridges is too large, then the silicon base layer will not be as flexible and will not form a curve. Locally flat areas of the block of silicon ridges would be too wide if the block of silicon ridges is too large. If the block of silicon ridges is too small, the silicon ridges and gratings may be deformed.

Figure 7:
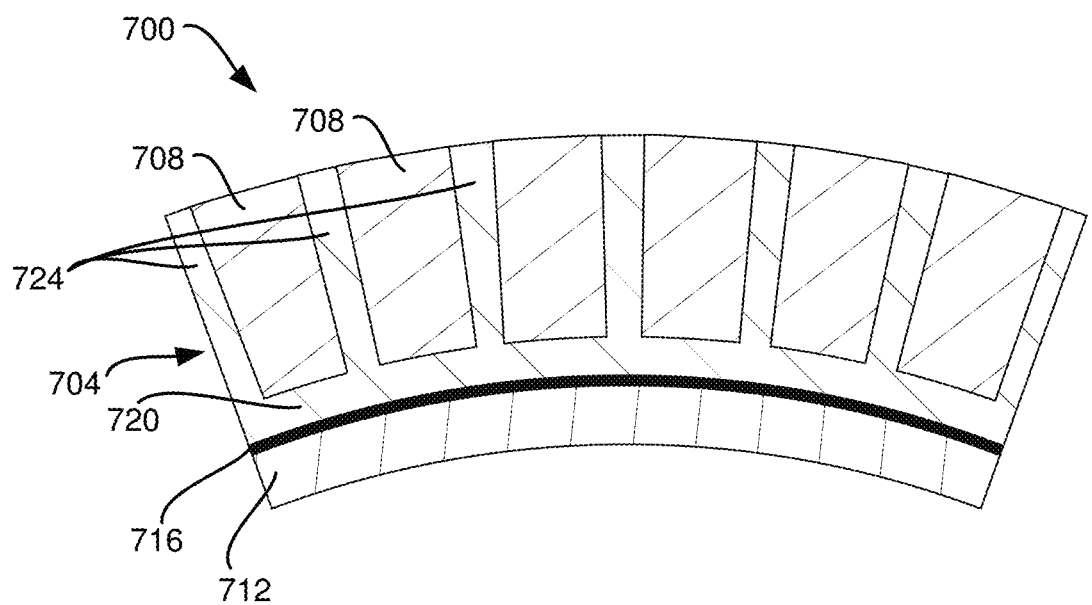
FIG. 7 is a schematic cross-sectional view of another embodiment.

In some embodiments, the silicon base layer may be attached to a curved surface before the metal layer is deposited on the silicon substrate. FIG. 7 is a schematic cross-sectional view of another embodiment of a grating 700. In this embodiment, a silicon substrate 704 with a silicon base layer 720 and a plurality of silicon ridges 724 are provided. The etch processes used in the above embodiments may be used to form the silicon ridges 724 (step 304). In this embodiment, the silicon base layer 720 is attached to the curved surface of the mounting substrate 712 by an adhesive 716 (step 312) before the metal is deposited. Metal 708 is deposited and fills trenches between the silicon ridges 724 (step 308). Polishing may be used to expose tops of the silicon ridges 724. Since there is only one metal line for each silicon ridge or for each trench, this embodiment does not reduce the pitch of the grating to half after the metal 708 is deposited.

In some embodiments, one or more layers of a dielectric, metal, photoresist or other material may be deposited on the silicon substrate. In addition, in some embodiments, a layer may be formed over the metallic deposition. Some embodiments provide a protective layer over the metallic deposition. Such a protective layer may fill trenches formed by the metallic deposition with a dielectric material of photoresist, spin-on glass, polydimethylsiloxane (PDMS), or epoxy.

Figure 8A:
FIGS. 8A-D are schematic cross-sectional views of a semiconductor substrate processed according to another embodiment.
Figure 8B:
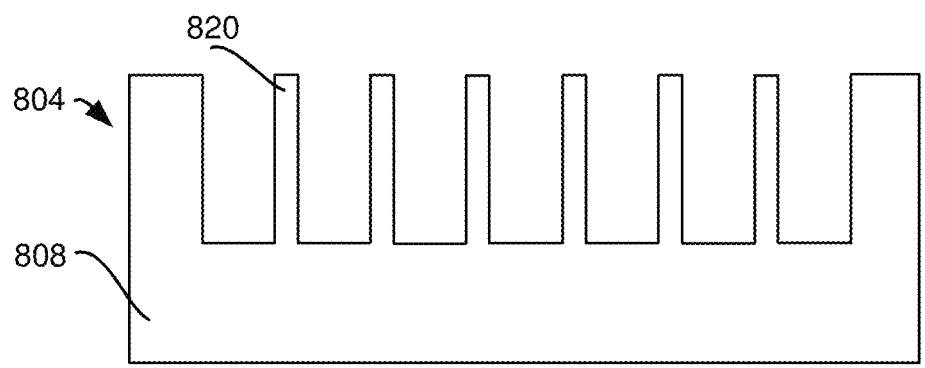
Figure 8C:
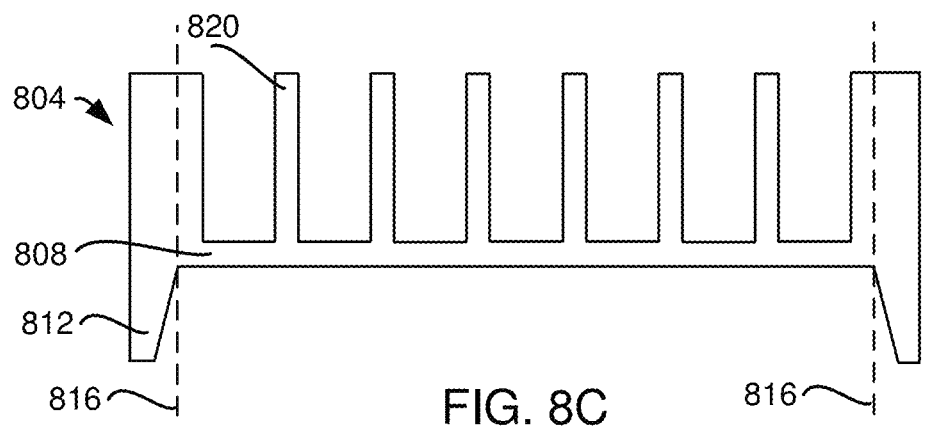
Figure 8D:
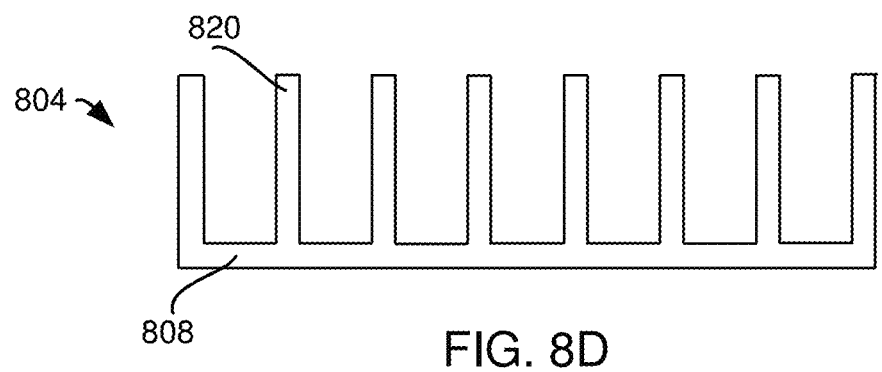

Various embodiments may be used to provide different methods of etching the substrate. FIG. 8A is a schematic cross-sectional view of a silicon substrate 804 that may be used for an embodiment. In this embodiment, the silicon substrate 804 is subjected to a patterned etch of a first side to form silicon ridges. FIG. 8B is a schematic cross-sectional view of the silicon substrate 804 where ridges 820 are formed on a first side of the silicon substrate 804. The second side of the silicon substrate 804 forms a thick base layer 808 connecting the silicon ridges 820. The base layer 808 is thinned by etching the second side of the silicon substrate 804. FIG. 8C is a schematic cross-sectional view of the silicon substrate 804 after the second side of the silicon substrate 804 has been etched to form a thin base layer 808. In this embodiment, feet 812 are formed in order to provide support during electroplating. The feet 812 are removed by cutting along slice lines 816. FIG. 8D is a schematic cross-sectional view of the silicon substrate 804 after the feet are removed. The electroplating deposition is not shown.

Figure 9A:
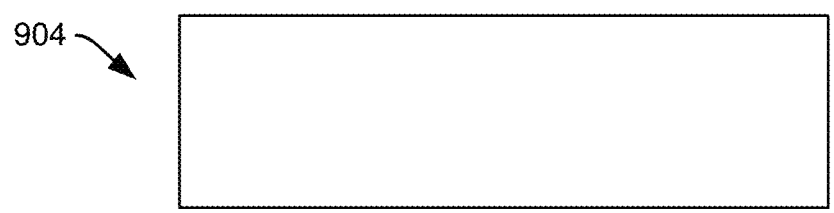
FIGS. 9A-D are schematic cross-sectional views of a semiconductor substrate processed according to another embodiment.
Figure 9B:
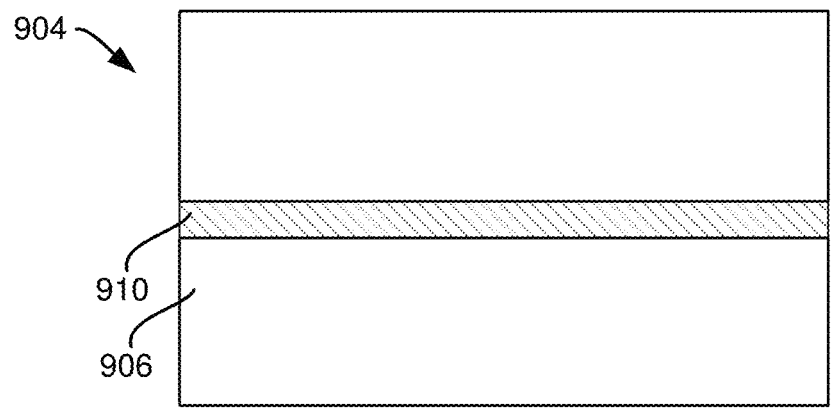
Figure 9C:
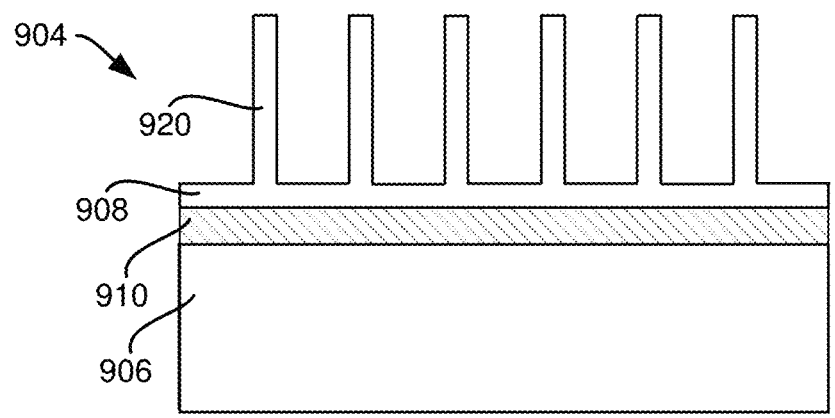
Figure 9D:
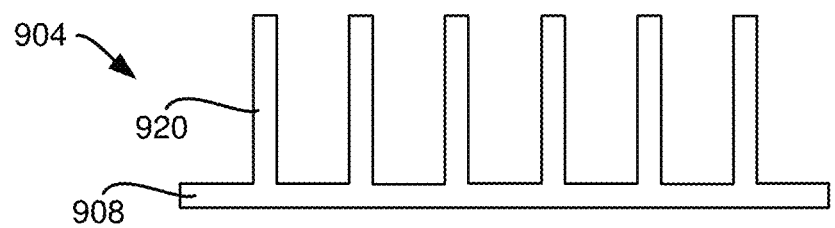

FIG. 9A is a schematic cross-sectional view of a silicon substrate 904 that may be used for another embodiment. In this embodiment, the silicon substrate 904 is bonded to a holder by a bond on a second side of the silicon substrate 904. FIG. 9B is a schematic cross-sectional view of the silicon substrate 904 bonded to a holder 906 by a bond 910 on a second side of the silicon substrate 904. The silicon substrate 904 is subjected to a patterned etch of a first side to form silicon ridges. FIG. 9C is a schematic cross-sectional view of the silicon substrate 904 where ridges 920 are formed on a first side of the silicon substrate 904. A thin base layer 908 connects the silicon ridges 920. The holder 906 and the bond 910 provide the support that is used to allow the etching to form a thin base layer 908. The holder 906 and the bond 910 are then removed. FIG. 9D is a schematic cross-sectional view of the silicon substrate 904 after the holder and bond are removed leaving the thin base layer 908 connected to the silicon ridges 920.

Figure 10A:
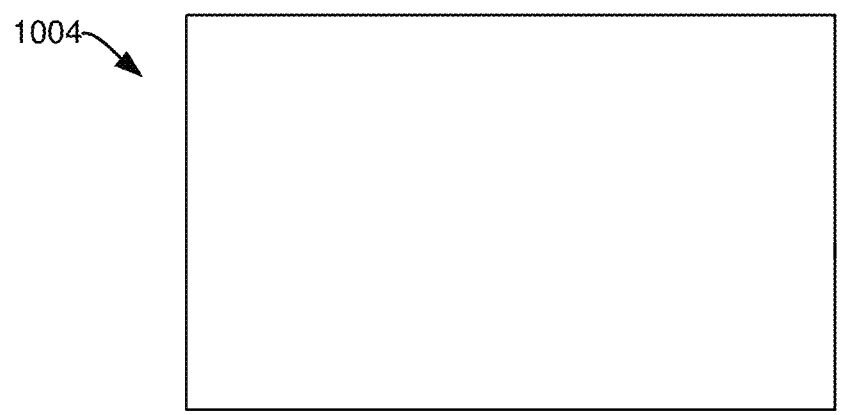
FIGS. 10A-D are schematic cross-sectional views of a semiconductor substrate processed according to another embodiment.
Figure 10B:
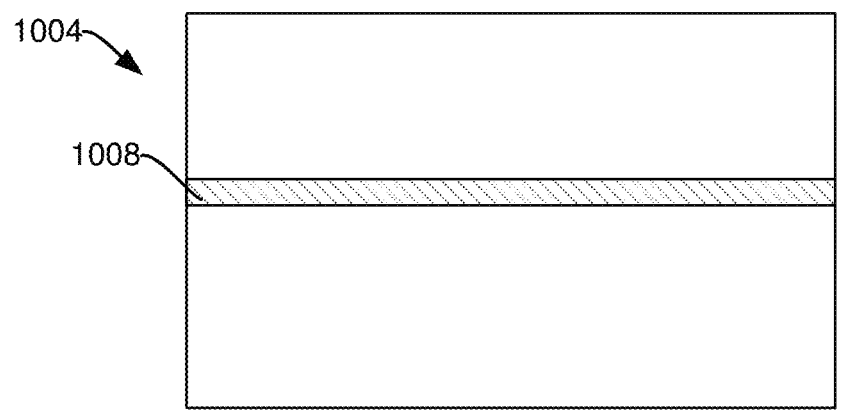
Figure 10C:
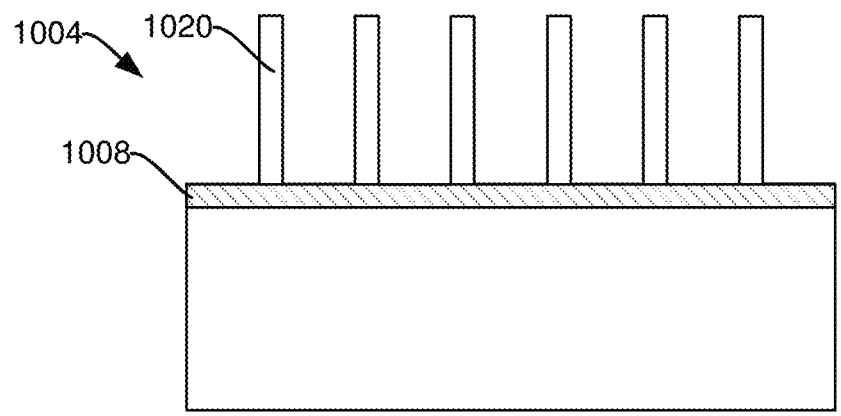
Figure 10D:
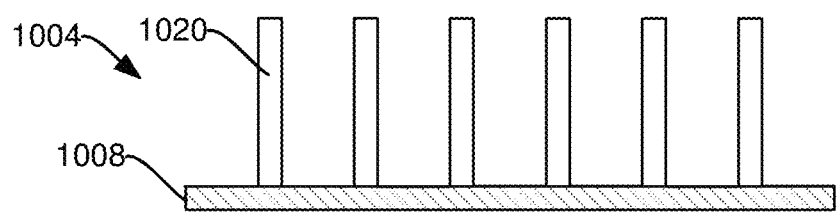

FIG. 10A is a schematic cross-sectional view of a silicon substrate 1004 that may be used for another embodiment. In this embodiment, a dielectric layer of silicon oxide is formed in the silicon substrate 1004. The embedded dielectric layer in a silicon substrate 1004 may be acquired as an SOI (silicon-on-insulator) wafer or may be formed using a process such as bonding a silicon wafer onto a surface oxidized silicon wafer or oxygen ion implantation into a silicon wafer. FIG. 10B is a schematic cross-sectional view of the silicon substrate 1004 with a dielectric layer 1008 formed in the silicon substrate 1004. The silicon substrate 1004 is subjected to a patterned etch of a first side to form silicon ridges. The etch selectively etches the silicon substrate 1004 with respect to the dielectric layer 1008 so that the dielectric layer 1008 is used as an etch stop. FIG. 10C is a schematic cross-sectional view of the silicon substrate 1004 where ridges 1020 are formed on a first side of the silicon substrate 1004 and where the dielectric layer 1008 is used as an etch stop. The dielectric layer 1008 connects the silicon ridges 1020. The second side of the silicon substrate 1004 is etched away, using the dielectric layer 1008 as an etch stop. FIG. 10D is a schematic cross-sectional view of the silicon substrate 1004 after the second side of the silicon substrate 1004 is etched away where the dielectric layer 1008 is used as an etch stop.

In this embodiment, the base layer 1008 is a dielectric layer, instead of a semiconductor. In this embodiment, the base layer 1008 is silicon-based, since the silicon oxide is formed from a silicon substrate. In other embodiments, the base layer may be silicon nitride, where the silicon nitride is formed from the silicon substrate and therefore is silicon-based. Such base layers are also silicon containing base layers. In the above embodiments, the ridges are silicon ridges. The ridges may be doped, but are silicon-based. Silicon-based objects are formed since silicon-based materials are able to be etched to provide high aspect ratios.

Figure 11:
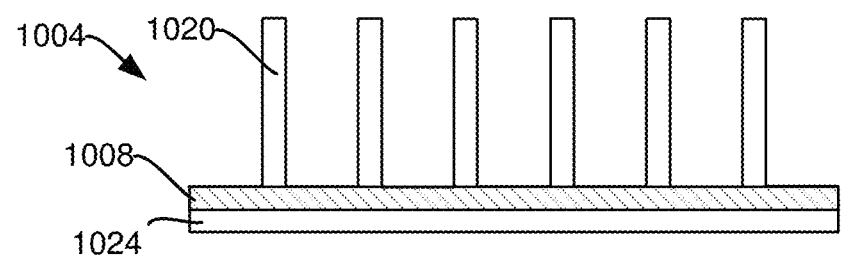
FIG. 11 is a schematic cross-sectional views of a semiconductor substrate processed according to another embodiment.

In another embodiment illustrated in FIG. 11, the same process is used to provide the silicon substrate as shown in FIGS. 10A-C. Instead of completely etching the second side of the silicon substrate 1004, using the dielectric layer 1008 as an etch stop, a silicon layer 1024 on the second side of the dielectric layer 1008 remains forming part of the base layer. The combined thicknesses of the dielectric layer 1008 and the silicon layer 1024 are less than 70 microns.

In various embodiments, because the base layer is flexible, the base layer may be attached to a curved surface by an adhesive. In some embodiments, the base layer may be attached to a surface while the surface is flat. Afterwards, the surface is curved, so that ultimately the base layer is attached to a curved surface. The curved surface may be concaved or convexed or a combination of concaved and convexed such as an S-shape. In some embodiments, the grating may use the silicon as the substrate, so that a metal layer is not used and therefore not deposited.

While this invention has been described in terms of several preferred embodiments, there are alterations, permutations, modifications, and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. An X-ray grating configured for use in an X-ray imaging apparatus, comprising:
    a silicon-based base layer;
    a plurality of silicon-based ridges on a surface of the silicon-based base layer, wherein the plurality of silicon-based ridges form a plurality of trenches wherein a trench of the plurality of trenches is between two silicon-based ridges of the plurality of silicon-based ridges; and
    a plurality of silicon-based bridges extending between adjacent silicon-based ridges across a trench between adjacent silicon-based ridges, wherein each silicon-based ridge of the plurality of silicon-based ridges is connected to at least one adjacent silicon-based ridge of the plurality of silicon-based ridges by at least one of a silicon-based bridge of the plurality of silicon-based bridges and wherein at least one of a plurality of four adjacent trenches does not have any silicon-based bridges.

2. The X-ray grating, as recited in claim 1, wherein the silicon-based base layer is curved with a radius of curvature of less than 50 cm.

3. The X-ray grating, as recited in claim 1, wherein every silicon-based ridge of the plurality of silicon-based ridges is connected to only one adjacent silicon-based ridge by at least one of a silicon-based bridge of the plurality of silicon-based bridges.

4. The X-ray grating, as recited in claim 1, wherein the plurality of silicon-based ridges have a height and width, wherein a ratio of the height to the width is greater than 5:1.

5. The X-ray grating, as recited in claim 1, wherein the silicon-based base layer has a thickness of no more than 70 microns.

6. The X-ray grating, as recited in claim 1 further comprising at least one metallic layer between the silicon-based ridges.

7. The X-ray grating, as recited in claim 6, wherein the at least one metallic layer comprises at least one of gold, lead, platinum, tungsten, or nickel.

8. The X-ray grating, as recited in claim 6, wherein the at least one metallic layer comprises a conformal layer formed over the plurality of silicon-based ridges.

9. The X-ray grating, as recited in claim 6, wherein the at least one metallic layer completely fills trenches between the plurality of silicon-based ridges.

10. The X-ray grating, as recited in claim 1, further comprising a mounting substrate with a curved surface, wherein the silicon-based base layer is attached to the curved surface of the mounting substrate by an adhesive.

11. An X-ray grating configured for use in an X-ray imaging apparatus, comprising:
- a silicon-based base layer with a thickness of no more than 70 microns; and
- a plurality of silicon-based ridges on a surface of the silicon-based base layer, wherein a trench of a plurality of trenches is between a pair of adjacent silicon-based ridges of the plurality of silicon-based ridges.

12. The X-ray grating, as recited in claim 11, further comprising a plurality of silicon-based bridges extending between adjacent silicon-based ridges, wherein each silicon-based ridge of the plurality of silicon-based ridges is connected to at least one adjacent silicon-based ridge of the plurality of silicon-based ridges by at least one of a silicon-based bridge of the plurality of silicon-based bridges and wherein every second, third, fourth, or fifth trench does not have any silicon-based bridges.

13. The X-ray grating, as recited in claim 11, wherein the plurality of silicon-based ridges have a height and width, wherein a ratio of the height to the width is greater than 5:1.

14. The X-ray grating, as recited in claim 11, wherein the silicon-based base layer is curved with a radius of curvature of less than 50 cm.

15. The X-ray grating, as recited in claim 11, further comprising a mounting substrate with a curved surface, wherein the silicon-based base layer is attached to the curved surface of the mounting substrate.

16. The X-ray grating, as recited in claim 15, wherein the silicon-based base layer is attached to the curved surface of the mounting substrate by an adhesive.

17. The X-ray grating, as recited in claim 11, further comprising a metallic deposition in the trenches of the plurality of trenches.

18. A method of forming an X-ray grating, comprising:
etching a silicon-based substrate to form a plurality of silicon-based ridges with trenches between the plurality of silicon-based ridges, and forming a base layer, wherein the plurality of silicon-based ridges are connected to the base layer and wherein the base layer has a thickness of no more than 70 microns.

19. The method, as recited in claim 18, wherein a plurality of bridges extend between adjacent silicon-based ridges, wherein each silicon-based ridge of the plurality of silicon-based ridges is connected to at least one adjacent silicon-based ridge of the plurality of silicon-based ridges by at least one of a bridge of the plurality of bridges and wherein every second, third, fourth, or fifth trench does not have any silicon-based bridges.

20. The method, as recited in claim 18, wherein the etching the silicon-based substrate, comprises etching trenches in a first side of the silicon-based substrate and etching a second side of the silicon-based substrate so that the base layer has a thickness of no more than 70 microns.

21. The method, as recited in claim 18, further comprising attaching the base layer to a curved surface.

22. The method, as recited in claim 21, wherein the attaching the base layer to a curved surface is by using an adhesive.

23. The method, as recited in claim 21, wherein the attaching the base layer to the curved surface forms a curve in the base layer with a radius of curvature of no more than 50 cm.

24. The method, as recited in claim 18, further comprising depositing a metal deposition in the trenches.

* * * * *